United States Patent [19]

Chernov

[11] 4,241,735
[45] Dec. 30, 1980

[54] ILEOSTOMY AND COLOSTOMY PLUG

[76] Inventor: Merrill S. Chernov, 4151 N. 32nd St., Phoenix, Ariz. 85018

[21] Appl. No.: 115,024

[22] Filed: Jan. 24, 1980

Related U.S. Application Data

[63] Continuation-in-part of Ser. No. 914,582, Jun. 12, 1978, abandoned.

[51] Int. Cl.³ .................. A61M 29/02; A61F 5/44
[52] U.S. Cl. .................................. 128/344; 128/283
[58] Field of Search ............... 128/1 R, 270, 283, 344

[56] References Cited

U.S. PATENT DOCUMENTS

| | | | |
|---|---|---|---|
| 2,507,858 | 5/1950 | Kegel | 128/2 |
| 3,154,077 | 10/1964 | Cannon | 128/344 |
| 3,216,420 | 11/1965 | Smith et al. | 128/283 |
| 3,447,533 | 6/1969 | Spicer | 128/1 R |
| 3,802,418 | 4/1974 | Clayton | 128/2 F |
| 3,826,242 | 7/1974 | Eggers | 128/1 R |
| 3,938,521 | 2/1976 | Ritota et al. | 128/283 |
| 4,030,500 | 6/1977 | Ronnquist | 128/283 |
| 4,050,461 | 9/1977 | Ruby | 128/283 |
| 4,117,847 | 10/1978 | Clayton | 128/348 |
| 4,148,317 | 4/1979 | Loyer | 128/263 |

FOREIGN PATENT DOCUMENTS 2431888 of 1976 Fed. Rep. of Germany ........... 128/283

*Primary Examiner*—Kyle L. Howell
*Assistant Examiner*—C. W. Shedd
*Attorney, Agent, or Firm*—Warren F. B. Lindsley

[57] ABSTRACT

A plug type closure for insertion into a body opening and employing a surrounding elongated balloon which when inflated expands to form a soft, non-erosive, relatively large surface contact in sealing engagement within the lumen of the body opening to prevent the unexpected release of odor and body waste materials.

6 Claims, 12 Drawing Figures

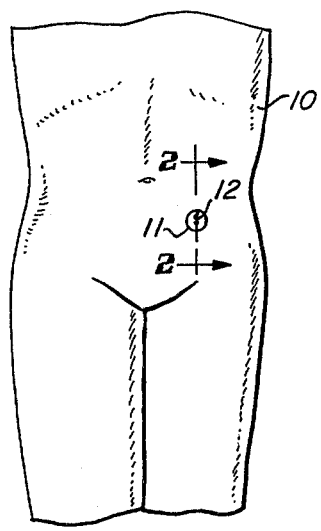
FIG-1
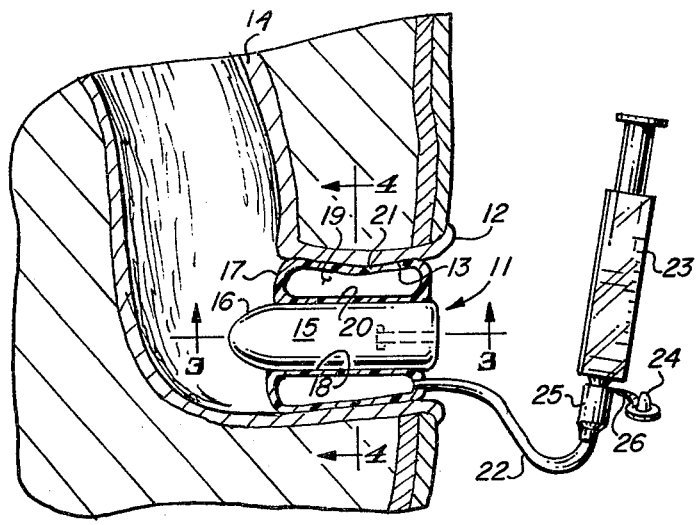
FIG-2
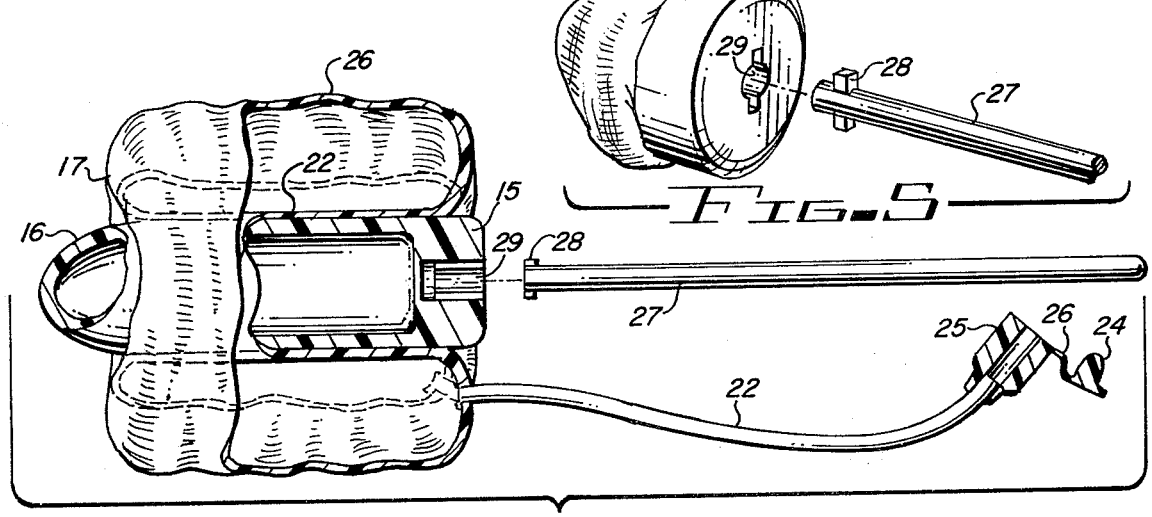
FIG-3
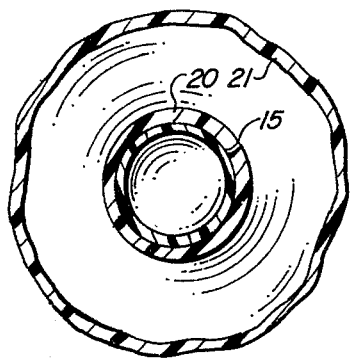
FIG-4
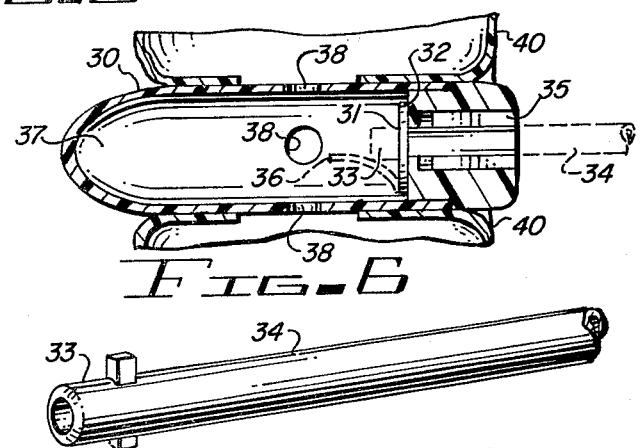
FIG-5
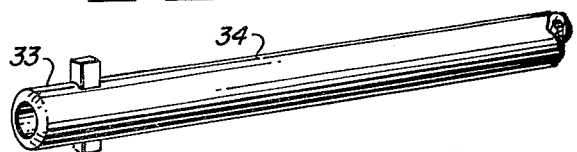
FIG-6
FIG-7

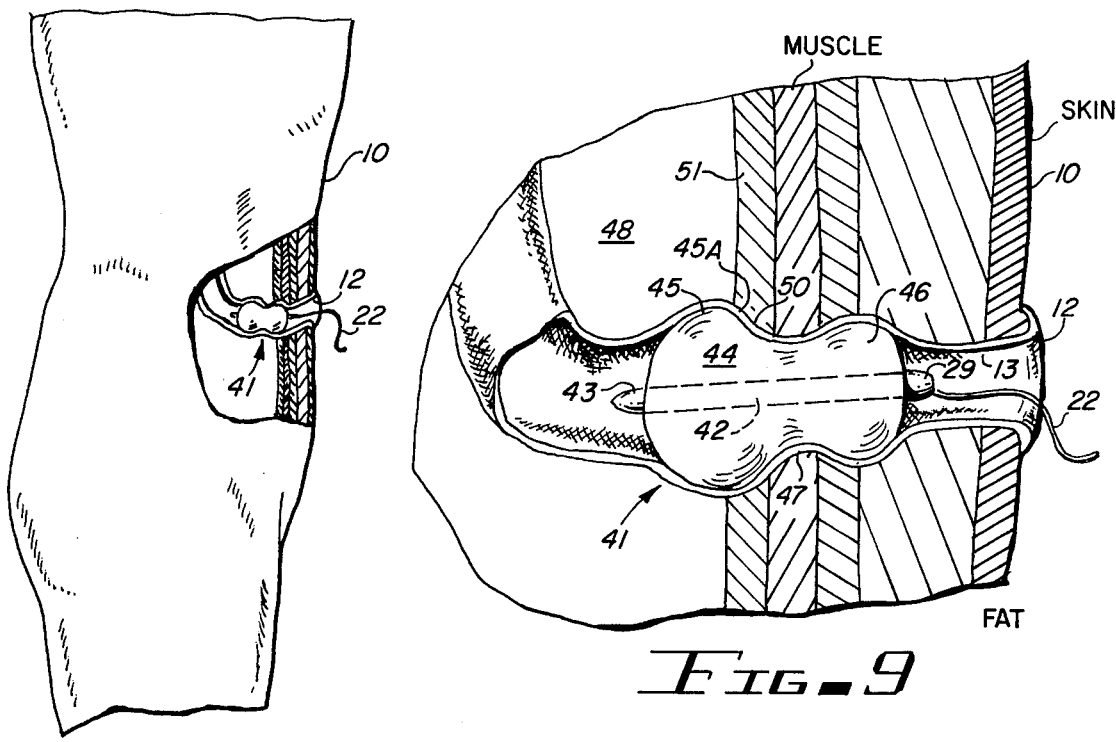
FIG-8
FIG-9
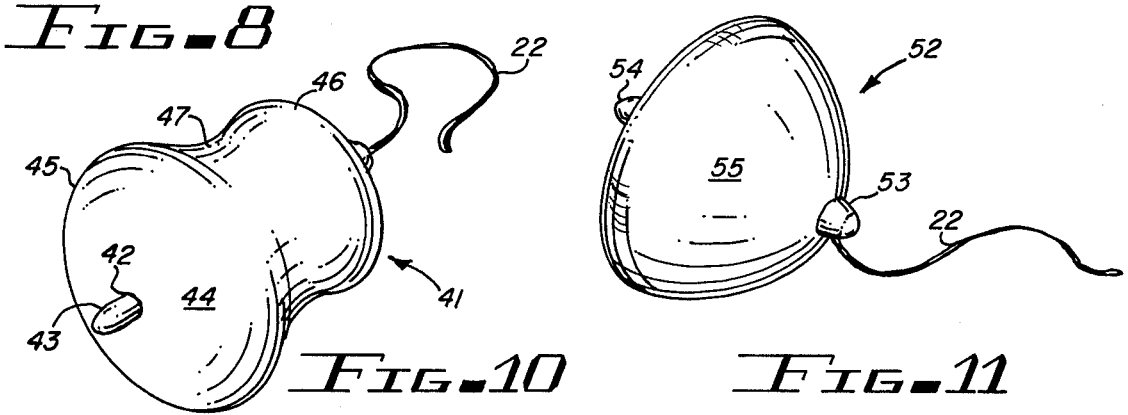
FIG-10
FIG-11
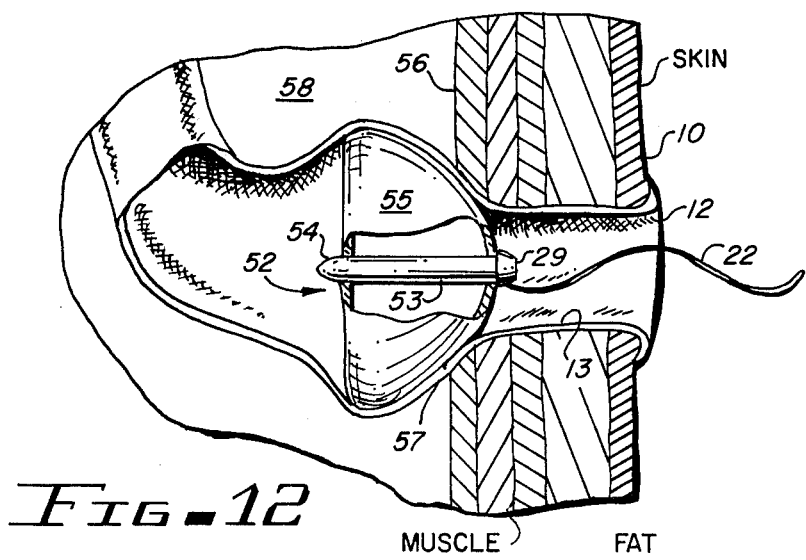
FIG-12

ILEOSTOMY AND COLOSTOMY PLUG

This application is a continuation-in-part of U.S. Patent Application, Ser. No. 914,582, filed June 12, 1978 and now abandoned and entitled ILEOSTOMY AND COLOSTOMY PLUG.

BACKGROUND OF THE INVENTION

This invention relates to surgical appliances for closing artificial body openings, such as artificial abdominal openings and the like, and in particular, to a surgical closure plug means adapted for ileostomy and colostomy use which may be dependably, conveniently and comfortably used by a patient without a belt, bag or any other unsightly attachment on the surface of the body and which will quickly rehabilitate a patient psychologically to a normal way of life and its pursuits within a minimum of time after the above related operations.

Generally, colostomy patients are those individuals who have had their lower bowels (rectum and anus) removed surgically due to cancer or other malignant infections of the colon or of like areas. The bowel (small or large) is, therefore, brought out by the surgeon through an aperture in the side of the abdominal wall of the patient and surgically attached to the outer skin for the purpose of serving as a means for the elimination of body wastes. In the medical field, the artificial body aperture or opening is termed a "stoma". Although a person can function quite well after this type of operation, there are no voluntary muscles or sphincter to control passage of body waste materials, liquids or gases. Pads, various receptacles and several means of bag attachments are either taped over the opening or attached thereto by means of a belt worn around the body to cover the stoma and to collect (not control) the escape of fecal waste or body liquid waste material. These means of waste elimination control are very inefficient and ineffective and present a great physiological problem to a recovering patient or to the rehabilitating of a recovered patient in that they must wear an external and clumsy outer bag to prevent the patient from soiling themselves.

Although plug type openings have been known, they have either applied pressure to a small area of the body opening thereby irritating the periphery of this opening, or have been difficult to apply and uncomfortable to wear and are not in use today.

DESCRIPTION OF THE PRIOR ART

U.S. Pat. No. 3,447,533 discloses a closure for body openings comprising a bulbous bladder member containing an air pocket which is deformed by a spring means and detachably locked in place to seal the body opening. This article uses a spring, the pressure of which may be dangerous to many users.

U.S. Pat. No. 3,802,418 discloses a colon catheter for removing and collecting waste colon material through the anal canal. One end of a hollow tube is inserted into the anal canal and held therein by an expandable member and limiting elements outside of the anal opening against the periseum.

U.S. Pat. No. 3,826,242 discloses a tubular member for insertion in the anal canal so that it engages the walls of the canal and the area around the rectal opening and is held in place during defecation.

U.S. Pat. No. 4,117,847 discloses a colon catheter having a hollow main tube insertable into the anal opening and held therein by an inflatable member located within the anal opening and limiting elements located outside of the anal opening and extending fore and aft from the main tube.

U.S. Pat. No. 4,148,317 discloses a tampon-applicator assembly comprising a generally cylindrical absorbent tampon having a proximal end and a distal end and a tampon bore within the tampon extending from the distal end toward the proximal end. A retainer is affixed to the distal end.

U.S. Pat. No. 3,938,521 discloses a collection bag for the collection of excretions from various body openings, both natural and surgical in nature, and includes an inflatable collar which is inserted into a body opening prior to inflation and which is then inflated to anchor itself within the opening.

U.S. Pat. No. 2,507,858 discloses an apparatus to indicate progressive exercise of injured sphincter muscles.

West German Pat. No. 2,431,888 discloses an artificial body opening closure employing an inflatable sheath surrounding its tubular body.

While the prior art suggests ways of controlling the ileostomy and colostomy, they are ineffective and not in use today.

SUMMARY OF THE INVENTION

In accordance with the invention claimed, a restrictive inflatable soft pressurized non-erosive balloon sealing surgical appliance is provided for insertion into and through the artificial body opening and into the end of the colon or duct to control and prevent the unexpected escape of gas, liquid and waste through the artificial body opening. This new surgical appliance may be made of various sizes and shapes to suitably seal and comfortably fit colostomies of various sizes yet not erode the bowel lining.

The method employed in this invention permits a patient to insert the appliance into the stoma or opening and adjust the radial expansion of the soft bulbous portion of the appliance against the internal walls of the colon and inside walls of the stoma for comfort and without causing erosion of the delicate bowel lining membrane. This appliance acts as a substitute for the voluntary muscles or sphincter of the rectum opening formerly used by the patient.

It is, therefore, one object of this invention to provide a new and improved closure appliance for artificial body openings so that patients can be free from wearing external collection bags or other appliances on the skin surface of their body wall, often glued on by irritating pastes, gells and other adhesive chemicals which often cause skin breakdown.

Another object of this invention is to provide a new and improved inflatable plug means for ileostomy and colostomy openings to prevent the unexpected release of waste material or fecal gases from the artificial opening.

A further object of this invention is to provide a new and improved closure appliance for body openings which can be worn without a belt or bag surrounding the body of the user below the skin surface of the patient.

A still further object of this invention is to provide a closure appliance which will comfortably seal within various sizes and shapes of artificial body openings spreading the engaging contact with the openings over a large surface portion thereof to prevent injury to the bowel's inner surface.

A still further object of this invention is to provide a new and improved closure appliance for artificial body openings which is positioned in the colon and at least partially within the abdominal cavity in an area of little if any nerve sensation for sealing from within the patient the artificial opening to prevent odor and uncontrollable, unexpected fecal or gas expulsions from being emitted from the opening.

A still further object of this invention is to provide a new and improved closure appliance for artificial body openings which is readily expandable by air pressure furnished by the patient using a syringe to cause a soft flexible surface of the appliance to bear against the internal surfaces of the body opening and preventing breakdown of the bowel inner surface.

A still further object of this invention is to provide a new and improved expandable closure appliance inserted in the colon within the stomach cavity for closing the artificial body openings from within the abdominal cavity and which employs an inflatable plug comprising an expandable bladder or balloon which seats against the internal orifice of the opening thereby preventing release of waste material from within the colon within the stomach cavity.

Another object of the invention is to provide a closure appliance for artificial body openings which is adapted to be easily removed, cleaned and sterilized.

Another object of the invention is to provide a closure appliance for artificial body openings which is expandable to conform to the contour of the inside walls and orifice of the opening and yet not injure the bowel's surfaces because of its low pressure.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWING

The present invention may be more readily described by reference to the accompanying drawing in which:

FIG. 1 illustrates a frontal view of the appliance after the appliance has been installed in an artificial body opening of a colostomy patient;

FIG. 2 is a partial sectional view of a human body and longitudinal sectional view of one embodiment of an appliance embodying the invention after the appliance has been sealably positioned and expanded within an artificial body opening;

FIG. 3 is a view of FIG. 2 part of which comprises a cross-sectional view of FIG. 2 taken along the line 3—3 and illustrating the insertion tool;

FIG. 4 is a cross-sectional view of FIG. 2 taken along the line 4—4;

FIG. 5 is a partial perspective exploded view of one end of the appliance showing the key slot for receiving the insertion tool;

FIG. 6 illustrates a modification of the appliance shown in FIGS. 1-5 wherein the inflating pressure is transmitted through the insertion tool into the plug and from the interior of the plug through an aperture into the inflating balloon;

FIG. 7 is a partial perspective view of the hollow insertion tool shown in FIG. 6;

FIG. 8 illustrates a side view partially broken away of the body of a patient with a modification of the appliance shown in FIG. 1-7 installed in the colon blocking the artificial opening of the patient from within the stomach cavity;

FIG. 9 is an enlarged partial view of the patient and appliance shown in FIG. 8;

FIG. 10 is an enlarged perspective view of the appliance shown in FIGS. 8 and 9;

FIG. 11 is a perspective view of a further modification of the appliances shown in FIGS. 1-10; and FIG. 12 is an enlarged partial view similar to FIG. 8 of the patient with the appliance shown in FIG. 11 seated against the inside orifice of the artificial opening in the abdominal wall.

DESCRIPTION OF THE PREFERRED EMBODIMENT

Referring more particularly to the drawings by characters of reference, FIG. 1 illustrates a diagrammatic illustration of the trunk portion of a human body 10 after a device or appliance 11 comprising the invention has been installed in a stoma or body opening 12 of a colostomy patient. This applicance or obturator, as shown in FIGS. 2-5, may be positioned in the passage 13 formed by opening 12 so as to project outwardly of the passage into the colon 14 of the patient.

The obturator comprises a tubular plug 15 which may be solid or hollow and having a rounded or torpedo configuration 16 at the colon protruding end. The plug which may be formed, for example, of a silicone latex material is sealably attached to the surface or walls of the lumen of the bowel and the area around the stoma by an inflatable and resilient bulbous ring-shaped balloon or member 17 secured around and along at least three-fourths of the length of the periphery 18 of plug 15. The member 17 may define a space 19 between membrane members 20 and 21 with the space 19 to be filled by air inserted thereinto through a hollow resilient tube 22 suitably connected to a pump such as a syringe 23. As noted, the free end of the tube 22 may be sealed closed by a plug type sealing cap 24 which may be attached to the collar end 25 of the tube.

As noted from FIG. 3, the ring shaped elongated balloon 17 is provided with an outer membrane member 21 which is formed to provide a soft outer surface 26 which forms a sealing engagement with the walls of the colon forming the opening 12 but without the harsh firmness of a rounded circular membrane surface. Even if surface 26 does engage the total surface 12, it will do so over a large surface area of passage 12 and with a gentle firmness thereby preventing breakdown of the bowl surface.

The appliance may be inserted into the opening 12 by an insertion tool 27 which is provided at one end with a laterally extending finger or key 28 which is arranged to matingly engage with a similarly shaped keyhold 29 in the closed end of the tubular plug 15 in a known manner. The tool is removed after the appliance has been inserted into the opening 19 either before or after the ring shaped balloon has been inflated to seal body opening 12.

It should be noted that the tube 22 is fixedly attached to appliance 10 and more particularly, balloon 17. When it is desired to remove the appliance from the body opening 12, it is merely necessary to remove sealing cap 24 from the opening in collar 25 in the well known manner and to allow the air captured in the space 19 of balloon 17 to exhaust to atmosphere. The appliance 10 may then be removed from the body opening 12 easily since the balloon 17 has then at least partially collapsed. By a gentle tug on tube 22, the appliance is removed from the body opening.

FIGS. 6 and 7 illustrate a modification of the structure shown in FIGS. 1-5 wherein plug 30 is provided with an opening 31 in its end 32 which is arranged for receiving the end 33 of a hollow insertion tool 34. This hollow insertion tool is provided for receiving at its other end a suitable source of air such as syringe 23.

As noted from FIG. 6, upon protrusion of end 33 of tool 34 into a suitable key slot 35 in end 32 of plug 30 and the pushing of a flap valve 36 closing the opening 31 in end 32 of plug 30, end 33 of insertion tool 34 moves into the hollow cavity 37 of plug 30 so that air under pressure moving through the hollow interior of tool 34 may flow into the hollow interior 37 of plug 30. From the interior 37 of plug 30, the air flows under pressure through one or more openings 38 spacedly arranged to extend through the outer periphery 39 of plug 30 into a resilient expandable balloon 40 having an outer surface of the same type as disclosed above for the appliance 10. This appliance works the same way and provides the same function as the appliance described above and shown in FIGS. 1-5.

FIGS. 8-10 disclose a modification of appliance 11 shown in FIGS. 1-7 embodied in passage 13 of the body opening 12 of the human body 10 wherein the appliance is inserted, inflated and deflated in the same manner and with the same appliance features, as shown and described for the appliance shown in FIGS. 1-7. Appliance 41 comprises a tubular plug 42 which may be solid or hollow having a rounded or torpedo shaped end 43 at the colon insertion end thereof. The plug which may be formed of silicone latex material is sealably attached to the surface or walls of the lumen of the bowels and the area around the stoma by an inflatable and resilient bulbous figure eight shaped balloon or member 44 secured along most of the length of the plug 42.

It should be noted that member 44 has a relatively large expandable portion 45 and a relatively small expandable portion 46 with a necked down portion 47 therebetween. This appliance is designed in the figure eight configuration such that the relatively large expandable portion 45 is moved into the colon or intestinal lumen in the abdominal cavity 48 so that its arcuate or conical configuration 45A will seat within the intestinal lumen against an orifice 50 formed by the expansion of portion 47 in the inner wall 51 of the abdominal cavity. In this position of appliance 41, the relatively smaller portion 46 thereof expands at least partially within and without the outside surface of wall 51 of the abdominal cavity, as shown in FIG. 9, to sealingly position the appliance in the artificial opening of the human body 10. In this position, appliance 41 is interlocked with the lining of the artificial body opening to sealingly close it with a soft cushioned and easily usable plug.

FIGS. 11 and 12 disclose a further modification of the appliances shown in FIGS. 1-10 wherein like parts of the appliances shown in FIGS. 1-10 are given the same reference characters. In FIGS. 11 and 12, the appliance 52 comprises a tubular plug 53 which may be solid or hollow having a torpedo shaped end 54 at the intestinal lumen insertion end. An inflatable and resilient bulbous cone shaped stopper 55 is provided along the length of plug 53 which when inflated, as shown in FIGS. 11 and 12, seats against the inside wall 56 of the abdominal cavity lining to distort it a bit for a seat therein around the entrance orifice 57 of the artificial opening in the human body 10. It should be noted that the bulbous portion 55 of the appliance is fully within the intestinal lumen and in turn the abdominal cavity 58 where there is no pain or nerve sensation to affect the comfort of the user when using this appliance.

In accordance with the teaching of this invention, FIGS. 8-10 disclose an appliance which not only seals with the artificial passageway into the colon of the patient, but simultaneously forms a seal with the abdominal cavity entranceway to seal and detachably interlock with this entranceway from the stomach side of the abdominal cavity. FIGS. 11 and 12 disclose an appliance which is positioned fully within the abdominal wall of the body so that when it is inflated and seated in position, it is in an area of the body that shields the patient from most discomforts in wearing it regardless of body movement. In this area, there is relatively no pain or nerve sensations to affect the user's comfort.

Although but a few embodiments of the present invention have been illustrated and described, it will be apparent to those skilled in the art that various changes and modifications may be made therein without departing from the spirit of the invention or from the scope of the appended claims.

What is claimed is:

1. A closure appliance for an artificial human body bowel opening extending through the abdominal wall comprising:
    an elongated tubular plug having a roundedly pointed end for extending into the artificial bowel opening through the abdominal wall and into the intestinal lumen; the other end of said plug being an insertion means for the appliance;
    a hollow, inflatable, elastic balloon secured annularly therealong to and surrounding most of the outer periphery of said plug;
    said balloon having at least one conical surface which when inserted in said artificial opening and then inflated, forms a sealing engagement with the inner surface of said artificial opening;
    a hollow tube connected to and in communication with the interior of said balloon at a location adjacent said other end of said plug, the other end of said tube being removably connectable to an inflating means for said balloon;
    said tube additionally providing a withdrawal means for said appliance; whereby when said balloon is deflated, pulling the tube will remove said appliance.

2. The closure appliance set forth in claim 1 wherein: said balloon when inflated comprises a figure eight configuration with said conical surface comprising one end of said figure eight configuration.

3. The closure appliance set forth in claim 1 wherein: said balloon comprises a cone shape configuration forming said conical surface.

4. The closure appliance set forth in claim 1 wherein: said insertion means comprises a slot at, said other end of said plug for receiving a tool for aiding in the inserting of said plug and attached balloon within the body opening.

5. The closure appliance set forth in claim 1 wherein: the outer surface of said balloon is provided with a smooth soft surface.

6. The closure appliance set forth in claim 2 wherein: said balloon when inflated comprising two conical configurations with said first conical configuration forming said first conical surface and said second conical configuration adapted to lie within said body opening for blockage thereof.

* * * * *